US009354434B2

(12) United States Patent
Kimura

(10) Patent No.: US 9,354,434 B2
(45) Date of Patent: May 31, 2016

(54) OPTICAL APPARATUS

(75) Inventor: Shigeharu Kimura, Yokohama (JP)

(73) Assignee: HITACHI, LTD., Tokyo (JP)

( * ) Notice: Subject to any disclaimer, the term of this patent is extended or adjusted under 35 U.S.C. 154(b) by 173 days.

(21) Appl. No.: 13/546,055

(22) Filed: Jul. 11, 2012

(65) Prior Publication Data

US 2013/0021616 A1 Jan. 24, 2013

(30) Foreign Application Priority Data

Jul. 19, 2011 (JP) ................................. 2011-157394

(51) Int. Cl.
| | |
|---|---|
| *G01B 9/02* | (2006.01) |
| *G02B 21/00* | (2006.01) |
| *G02B 27/09* | (2006.01) |
| *G01N 21/47* | (2006.01) |
| *G01J 3/453* | (2006.01) |
| *G01J 9/02* | (2006.01) |
| *G01J 3/447* | (2006.01) |

(52) U.S. Cl.
CPC ........ *G02B 21/0072* (2013.01); *G01B 9/02038* (2013.01); *G01J 3/447* (2013.01); *G01J 3/453* (2013.01); *G01J 9/02* (2013.01); *G01N 21/4795* (2013.01); *G02B 21/0056* (2013.01); *G02B 21/0068* (2013.01); *G02B 27/0988* (2013.01)

(58) Field of Classification Search
CPC ............. G01B 27/0988; G01B 9/0209; G01B 2290/70; G01B 9/02038; G01N 21/21
USPC .......................... 356/364, 369–370, 491, 495; 369/53.11–53.45
See application file for complete search history.

(56) References Cited

U.S. PATENT DOCUMENTS

| | | | |
|---|---|---|---|
| 5,590,110 A | 12/1996 | Sato | |
| 5,883,717 A * | 3/1999 | DiMarzio et al. | ............. 356/491 |
| 6,721,094 B1 | 4/2004 | Sinclair et al. | |
| 2008/0018966 A1* | 1/2008 | Dubois et al. | ..................... 359/9 |

(Continued)

FOREIGN PATENT DOCUMENTS

| | | |
|---|---|---|
| JP | 4-125826 | 4/1992 |
| JP | 07-192297 | 7/1995 |

(Continued)

OTHER PUBLICATIONS

C. J. R. Sheppard et al., Image formation in the scanning microscope, Optical Acta, 1977, pp. 1051-1073, vol. 24, No. 10.

(Continued)

*Primary Examiner* — Michael A Lyons
*Assistant Examiner* — Dominic J Bologna
(74) *Attorney, Agent, or Firm* — Baker Botts L.L.P.

(57) ABSTRACT

Provided is an optical apparatus characterized in that alight from a light source is split to a first light and a second light, and the first light is focused onto an observation object, that an optical filter having a light shielding region for high resolution is disposed in at least one optical path selected from optical paths of the first light, second light and response light from the observation object, that an interference light formed by causing interference between the response light and the reference light in polarized states different from each other is split to multiple beams, and desired amplitude information signals are obtained from the multiple beams through a phase plate and a polarization plate to increase intensity of the second light, whereby the signal to noise ratio is improved.

18 Claims, 15 Drawing Sheets

(56) References Cited

U.S. PATENT DOCUMENTS

| | | |
|---|---|---|
| 2008/0067321 A1 | 3/2008 | Miyamoto et al. |
| 2008/0205246 A1* | 8/2008 | Shimano et al. ......... 369/112.16 |
| 2008/0291463 A1* | 11/2008 | Milner et al. ................. 356/491 |
| 2010/0027026 A1* | 2/2010 | Miyata .......................... 356/487 |
| 2010/0039917 A1 | 2/2010 | Ide |
| 2010/0059696 A1* | 3/2010 | Heintzmann et al. ......... 250/550 |
| 2010/0166293 A1* | 7/2010 | Sugita et al. ................. 382/154 |
| 2011/0058175 A1* | 3/2011 | Suehira ........................ 356/450 |

FOREIGN PATENT DOCUMENTS

| | | |
|---|---|---|
| JP | 11-45058 | 2/1999 |
| JP | 2008-065961 | 3/2008 |
| JP | 2010-044832 | 2/2010 |

OTHER PUBLICATIONS

Office Action issued in Japanese Patent Application No. 2011-157394 on Jul. 22, 2014.

* cited by examiner

US 9,354,434 B2

OPTICAL APPARATUS

CLAIM OF PRIORITY

The present application claims priority from Japanese patent application JP 2011-157394 filed on Jul. 19, 2011, the content of which is hereby incorporated by reference into this application.

FIELD OF THE INVENTION

The present invention relates to an optical apparatus requiring an optical resolution. More particularly, the present invention relates to an optical apparatus configured to focus a light beam and acquire a signal by relatively changing an irradiation position of the light beam with respect to an observation object.

BACKGROUND OF THE INVENTION

There exists a confocal scanning microscope as a technology for improving the resolution of the optical microscope. There are two types of the optical system: a reflective type and a transmission type. For better understanding of the optical system, the microscope of the transmission type will be explained. FIG. 8 is a schematic diagram of a transmission type optical system. Light from a light source 101 is irradiated to a pin hole 205 to get a point light source. In reality, the point light source is not a perfect point light source, since a pin hole of a finite size is used. A light from the pin hole is focused onto an observation object 202 through an objective lens 201. The observation object 202 can be scanned in a three dimensional direction by a scanning mechanism 102 such as a voice coil. The light, which has passed through the observation object, passes through a detection lens 203 and is focused onto a pin hole 204. The light, which has passed through the pin hole 204, is detected by a light detector 103, and its signal is displayed on a display device 104 configured to display an image associated with a scanned position of the observation object. It is known that lateral resolution of the confocal scanning microscope depends on the size of the pin hole 204. Smaller the pin hole, higher the resolution. Reversely, larger the pin hole, lower the resolution and closer to a resolution of a conventional optical microscope which is not of the scanning type. The conventional optical microscope herein referred is a non-scanning type microscope which irradiates a wide range of an observation object and forms an image from a light which has passed through an objective lens from the observation object. FIG. 9 shows point spread functions of the conventional optical microscope and a confocal scanning microscope having a pin hole of ultra minimum size. Abscissa v is expressed in a normalized optical unit defined as $v=2\pi \cdot x \cdot NA/\lambda$, in which NA represents the number of apertures of the objective lens 201 and the detection lens 203, and both of the lens are assumed to have a same NA. Further, x represents a coordinate vertical to the optical axis or a lateral coordinate, and $\lambda$ represents the wavelength of light. A point spread function 131 of the confocal scanning microscope is narrower than a point spread function 130 of the conventional optical microscope, from which it is understood that the resolution has been improved.

A non-patent document (C. J. R. Sheppard and A. Choudhury, "Image Formation in the Scanning Microscope", Opt. Acta, Vol. 24, 1051-1073 (1977)) discloses a method of shielding a central portion of the beam for further improving the resolution. In an optical system of the confocal scanning microscope shown in FIG. 10, a circular light shielding plate 229 having a center thereof on the optical axis is inserted in an optical path of the light which has passed through an observation object 202. The circular light shielding plate 229 disposed in such a manner eliminates low frequency components in a spatial frequency region of the light emitted from the observation object 202, and thereby improves the resolution.

SUMMARY OF THE INVENTION

In the confocal scanning microscope shown in FIG. 8, the resolution can be improved by reducing the size of pin hole, but deterioration of the signal to noise ratio is not avoidable since the amount of light passing through the pin hole becomes smaller. The light shielding plate 229 in FIG. 10 disposed for further improving the resolution also results in reducing the light amount. That is, as a higher resolution in a microscope optical system is sought, the amount of detected light becomes smaller. In general, such problems are addressed by increasing output power of the light source. However, in a case where damage to an observation object by the incident light is not allowed, output power of the light source cannot be increased.

The problem to be addressed by the present invention is to achieve both a high resolution and a high signal to noise ratio even when the amount of light irradiated to the observation object is small.

To address the foregoing problem, an optical apparatus adopted according to the present invention is capable of splitting the amplitude of interference between a beam emitted from the observation object and the reference light in different polarization states. The optical apparatus further comprises an optical filter disposed in at least one location and including a light shielding filter for a higher resolution.

The present invention is achieved by an optical apparatus comprising a splitting optical system configured to split a light emitted from a light source to an irradiation light (first light) directed toward an observation object and a reference light (second light), a focusing optical system configured to focus the irradiation light onto the observation object, a detection optical system configured to detect a response light such as a light reflected from the observation object and a light passing through the observation object, a polarization optical element configured to turn response and reference lights into different polarization states, an optical filter disposed in at least one location selected from optical paths of irradiation, response and reference lights, an element configured to superpose response and reference lights to each other, an optical element configured to split a superposed synthetic response light, different polarization filters each disposed in optical paths of the divided synthetic response lights, detectors each configured to detect a split synthetic response light, and an electronic circuit configured to process signals received from respective detectors.

According to an aspect of the present invention, intensity of the response light subjected to an optical filtration can be amplified by increasing intensity of the reference light, and thereby the signal to noise ratio can be improved. Further, an optical filter disposed in an optical path of the reference light prevents a decrease of the amount of the response light, so that an optical adjustment can be made easily and the resolution can be improved. In this case, the signal to noise ratio also can be further improved by increasing intensity of the reference light.

DETAILED DESCRIPTION OF THE PREFERRED EMBODIMENTS

Hereinafter, preferred embodiments of an optical apparatus according to the present invention are described with reference to the drawings.

First Embodiment

Figure 1:
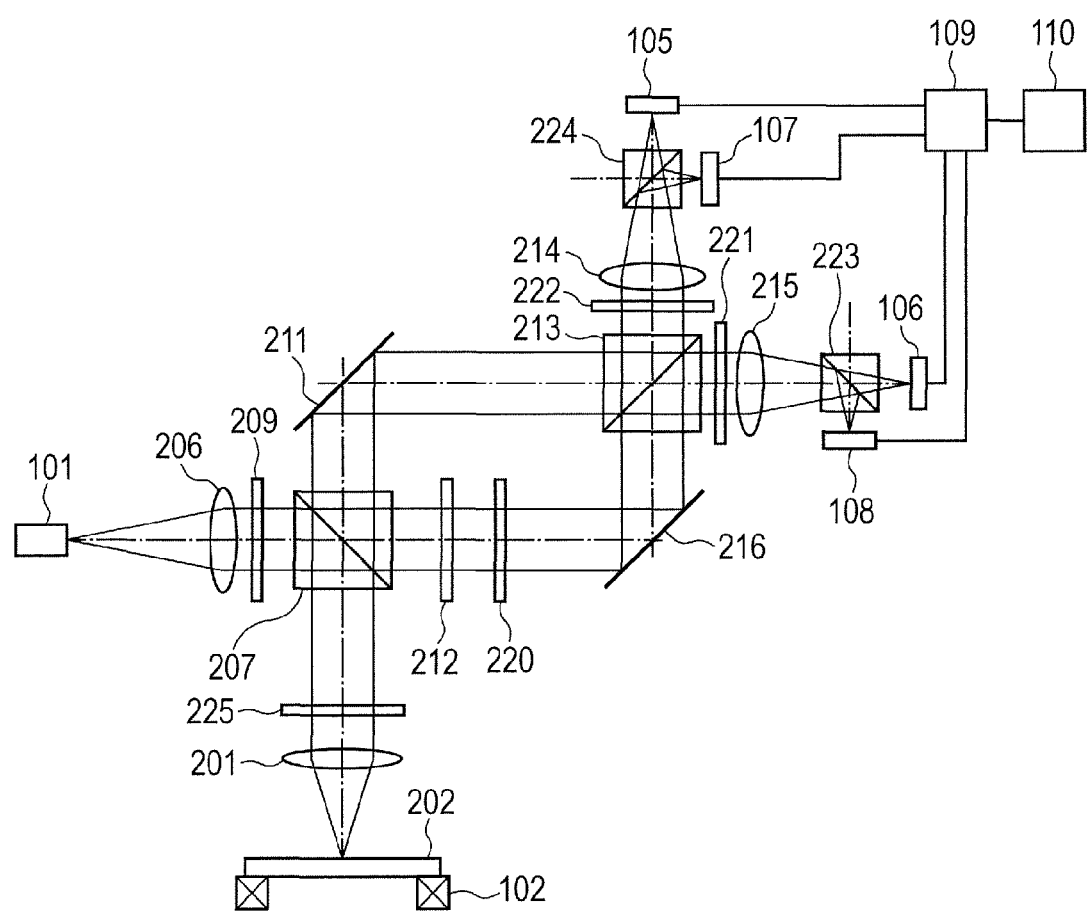
FIG. 1 shows an optical system according to the present invention.

FIG. 1 shows an optical apparatus according to an aspect of the present invention. FIG. 1 shows an optical apparatus comprising an optical filter 220 disposed in the light flux of the reference light. 101 represents a laser light source configured to convert an emitted s-polarized light to a parallel light through a collimator lens 206. A light emitted from the laser light source has a coherence length of about 5 mm or longer, so that interference is apt to occur even when there is an optical path length difference. This eliminates necessity of an optical path length adjustment mechanism. 207 represents a polarization beam splitter configured to reflect an s-polarized light and transmits a p-polarized light. A $\lambda/2$ plate 209 disposed between the collimator lens 206 and the polarization beam splitter 207 is rotatable and serves as a light amount alteration means by adjusting the amount of lights reflected or transmitted by the polarization beam splitter. The s-polarized light, which has passed through the $\lambda/2$ plate, is reflected by the polarization beam splitter and converted to a circularly polarized light by a $\lambda/4$ plate 225. Thereafter, the light is focused onto an observation object 202 through an objective lens 201. The observation object can be scanned by a scanning mechanism 102. According to the present embodiment, a method of scanning the observation object itself is adopted in order to avoid complexity of an optical system. However, the method is not limited thereto. A method comprising an optical system configured to scan a light focusing spot itself may be used. Further, the present embodiment is described on the basis of an optical system configured to detect a light reflected from the observation object, but an optical system transmitting a light through the observation object may be used. A light reflected from the observation object returns to the objective lens 201 and passes through the $\lambda/4$ plate 225, where the light turns to a p-polarized light. The p-polarized light passes through the beam splitter 207, is reflected by a reflecting mirror 211 and enters a half beam splitter 213.

Figure 2:
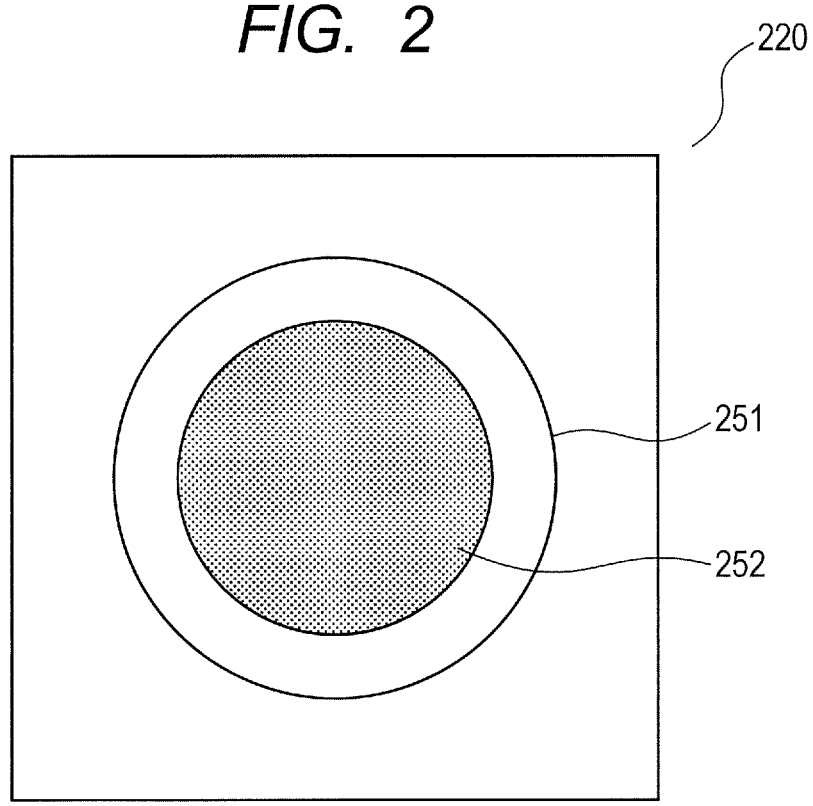
FIG. 2 shows a shape of a light shielding plate.

A p-polarization component of the light, which has passed through the $\lambda/2$ plate, passes through the polarization beam splitter 207 and turns to an s-polarized light at the $\lambda/2$ plate 212 having the optical axis thereof tilted by 45 degrees. Thereafter, the light is partially shielded or reduced by an optical filter 220 and enters the half beam splitter 213 through a reflecting mirror 216. A shape of the optical filter 220 is shown in FIG. 2. 251 represents a beam shape of the reference light, in which a shielding region 252 is arranged so as to shield a central part of the beam. A light shielding plate can be fabricated by vapor deposition of a circular thin metal film made of chrome on a glass substrate through which a light passes. The optical filter 220 causes a light only in a peripheral region of the beam to be involved in the interference to improve the resolution. To improve the resolution sufficiently, it is preferable that the radius of the light shielding region is 70% or more of the effective diameter of the beam. Although the light amount decreases due to an increased light-shielding ratio, the S/N ratio can be improved by increasing intensity of the reference light. Therefore, there is no problem even if the light-shielding ratio is increased. Accordingly, it is preferable that intensity of the reference light is adjusted so as to be higher than intensity of a detected light.

Lights having polarizing directions different from each other enter the half beam splitter 213 from two directions. There, respective lights are split into two directions, and an interference light is emitted in two directions. The interference light, which has passed through the half beam splitter 213 in the right direction in FIG. 1, passes through the $\lambda/2$ plate having the optical axis thereof tilted by 22.5 degrees and is focused on a detector disposed at a focal position by a condenser lens 215. According to the present embodiment, the $\lambda/2$ plate 221 is disposed in front of the condenser lens 215, but there is no problem even if $\lambda/2$ plate 221 is disposed right after the condenser lens 215. A polarization beam splitter 223 is disposed in the optical path in front of the detector configured to decompose the interference light to s-direction and p-direction components. Each of the decomposed lights is detected by a detector 106 and a detector 108. Here, the observation object is assumed to be a point object on the optical axis. When assuming that complex amplitudes of the reflected light from the observation object and reference light are A and R respectively, and a differential signal of the detector 106 and detector 108 is Ic, $Ic = \alpha |\cdot| R | \cos(\theta)$. $\alpha$ represents coefficients including the signal amplitude, detector efficiency, and the like, and $\theta$ represents a phase difference between the reflected light from the observation object and reference light. Further, the interference light, which has passed through the half beam splitter 213 in an upward direction in the figure, passes through a λ/4 plate 222 having the optical axis tilted by 45 degrees. The interference light focused by a condenser lens 214 is detected by detectors 105 and 107. Also in this case, the λ/4 plate 222 may be disposed right after the condenser lens 214. A polarization beam splitter 224 disposed between the condenser lens 214 and the polarization beam splitter 224 splits the interference light to s-polarized and p-polarized lights. Thereafter, the lights are detected by respective detectors. Here, when assuming that a differential signal of detectors 105 and 107 is Is, Is=α|A|·|R|sin(θ). Ic and Is contain detected interference components only. A calculation device 109 calculates I=Ic²+Is²=α²|A|²|R|² (Formula 1). I represents a variable proportionate to the square of amplitudes of reflected and reference lights and is not affected by the phase difference between the beams. 110 represents a display device configured to display by associating a scanning position of the observation object 202 and a display position to each other. According to the present embodiment, signals from four detectors are used. However, interference components may be calculated using three detectors out of the four, in which case, it is preferable to use a calculator such as a microcomputer.

Assuming that magnification of the optical system is "M" and a point object serving as the observation object exists at a position apart by distance "a" from the optical axis, a point spread is formed on each of the four detectors with the center thereof located apart by Ma from the optical axis. At the same time, the reference light has a point spread with the center thereof at the optical axis. Assuming that an amplitude point spread of a standard optical system having the center thereof located at Mx is h(Ma) and an amplitude point spread of the reference light is g(O), an output signal I(a) is expressed by I(a)=α²|∫∫h(Ma)g(O) dxdy|². Surface integration is performed by the detectors. This integration effect improves the resolution.

Figure 11:
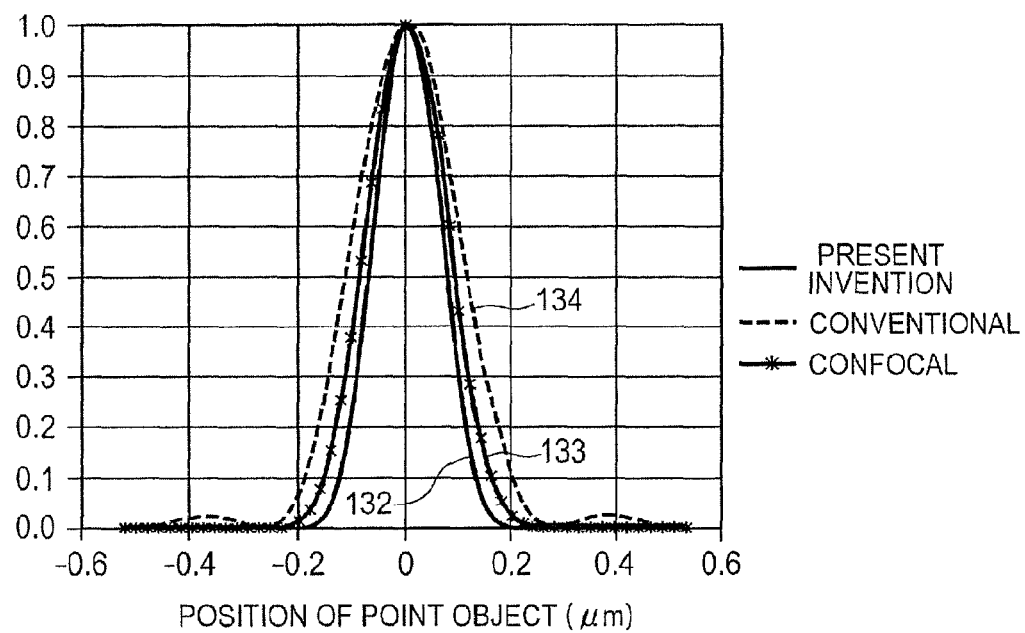
FIG. 11 shows point spread functions of a conventional optical microscope, a confocal scanning microscope and an optical apparatus according to the present invention.

FIG. 11 shows calculated point spread functions. With NA of the objective lens being 0.85, a point object having a diameter of 0.05 μm was moved on a focus surface vertically relative to the optical axis. A light shielding plate was disposed in the reference light to shield the light in an inner 80% region of the effective diameter. The amount of light irradiated onto the observation object was same as the amount of the reference light. For the purpose of comparison, FIG. 11 shows point spread functions of a confocal scanning microscope and a conventional microscope calculated under a same condition. A light shielding plate is not disposed in the confocal scanning microscope and the standard microscope. The point spread of the optical system according to the present invention is narrower as indicated by a solid line 132. From this, it is understood that a resolution of the optical system is better than resolutions indicated by point spread functions of the confocal scanning microscope (solid line with ×133) and the standard optical system. Further, according to the present embodiment, the resolution is improved by filtering the reference light through the light shielding filter, although a light reflected from the observation object is not subjected to light shielding. Accordingly, the optical system according to the present embodiment may be configured into a standard optical system by shielding the reference light, so that co-existence of both optical systems is easily affordable. When the amount of the light reflected by the observation object is small, the signal intensity can be increased by increasing intensity of the reference light |R|² as shown in Formula 1, whereby the signal to noise ratio can be improved.

Figure 12:
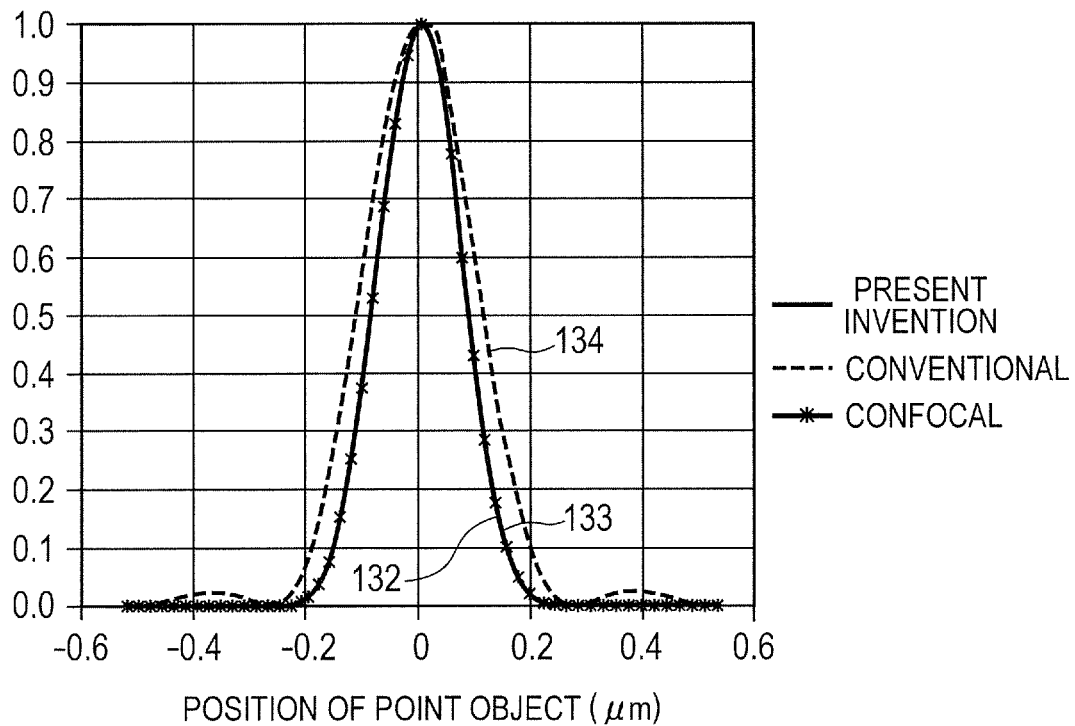
FIG. 12 shows point spread functions of a conventional optical microscope, a confocal scanning microscope and an optical apparatus according to the present invention without a light shielding plate.

When the light shielding region provided in the reference light is reduced, a point spread function 132 according to the present invention becomes same as a point spread function (133) of the confocal scanning microscope as shown in FIG. 12, resulting in deteriorating of the resolution. However, the deteriorated resolution is still same as a resolution of the confocal scanning microscope and better than a resolution of the standard microscope as well. Further, the optical system according to the present invention provides no pin hole in front of a detector unlike a confocal scanning microscope, so that a significant decrease of the light amount can be avoided and the signal to noise ratio can be further improved by increasing intensity of the reference light.

In the embodiments shown in FIGS. 3 to 6, optical filters are disposed at different locations.

Figure 3:
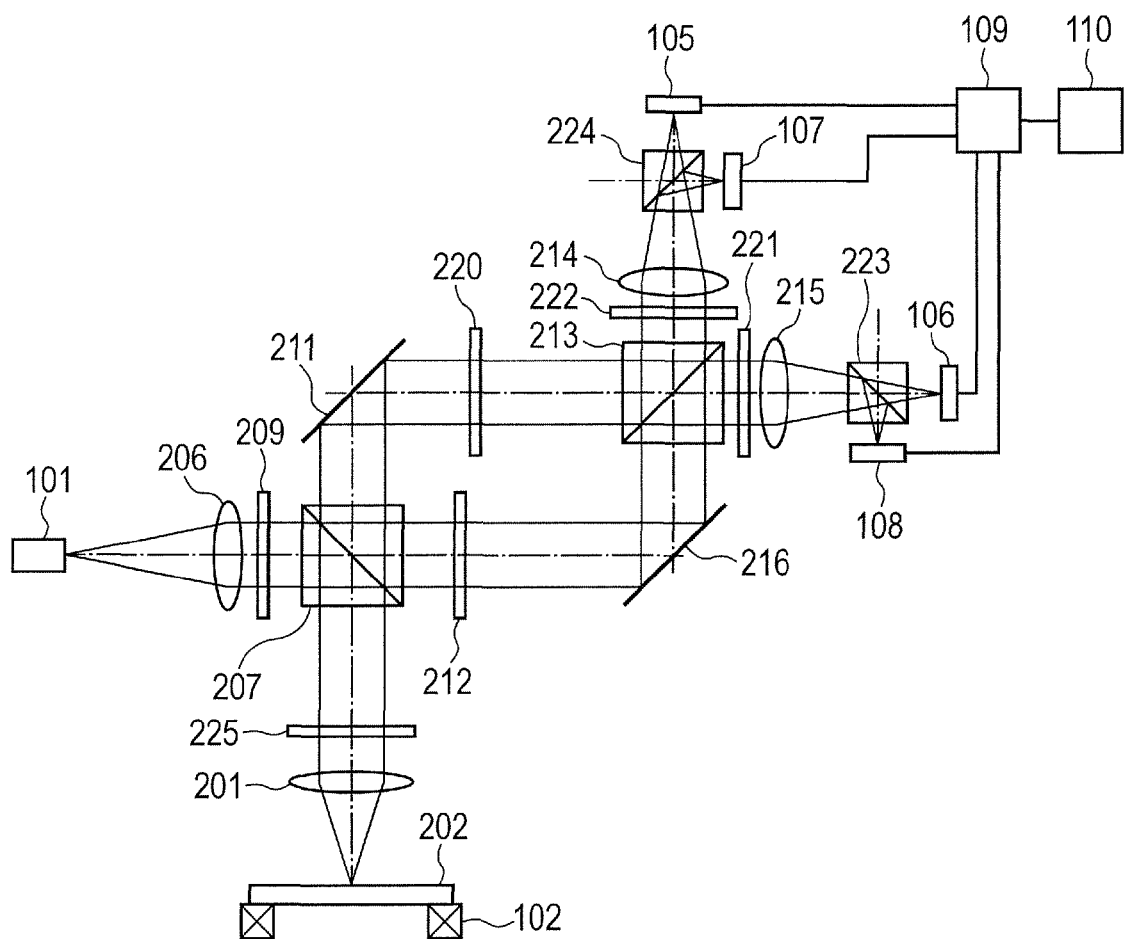
FIG. 3 shows an optical system according to the present invention.

FIG. 3 shows a light shielding plate 220 disposed as an optical filter in an optical path of a light reflected by the observation object. The resolution can be improved to a same extent as the first embodiment if a light shielding plate same as the one shown in FIG. 1 is used. However, it is more preferable to dispose an optical filter 220 in the light flux of the reference light as shown in FIG. 1 to prevent the amount of the response light from decreasing.

Figure 4:
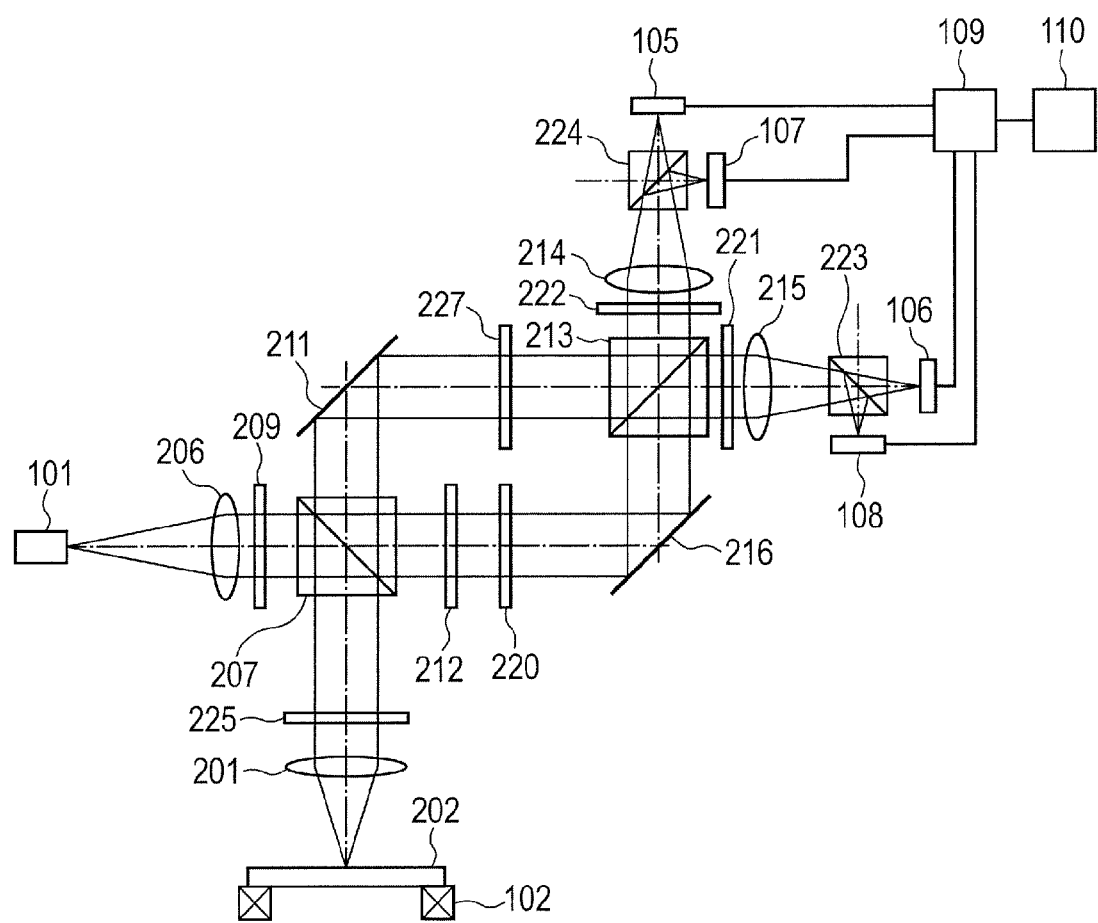
FIG. 4 shows an optical system according to the present invention.

FIG. 4 shows light shielding plates 220 and 227 disposed respectively in light paths of the reference light and a light reflected by the observation object. If the center size of all of the light shielding plates relative to the effective diameter is same as the size of the light shielding plate shown in FIG. 1, a resolution same as shown in FIG. 1 is obtained. When desired to suppress the amount of light entering detectors to an unsaturated extent, use of two light shielding plates such as those according to the present embodiment is effective. In an optical system shown in FIG. 4 in which two light shielding plates are disposed, if there is a difference in the shape between the light shielding plates, the size of a sum region determined by the two light shielding regions affects the resolution.

Figure 5:
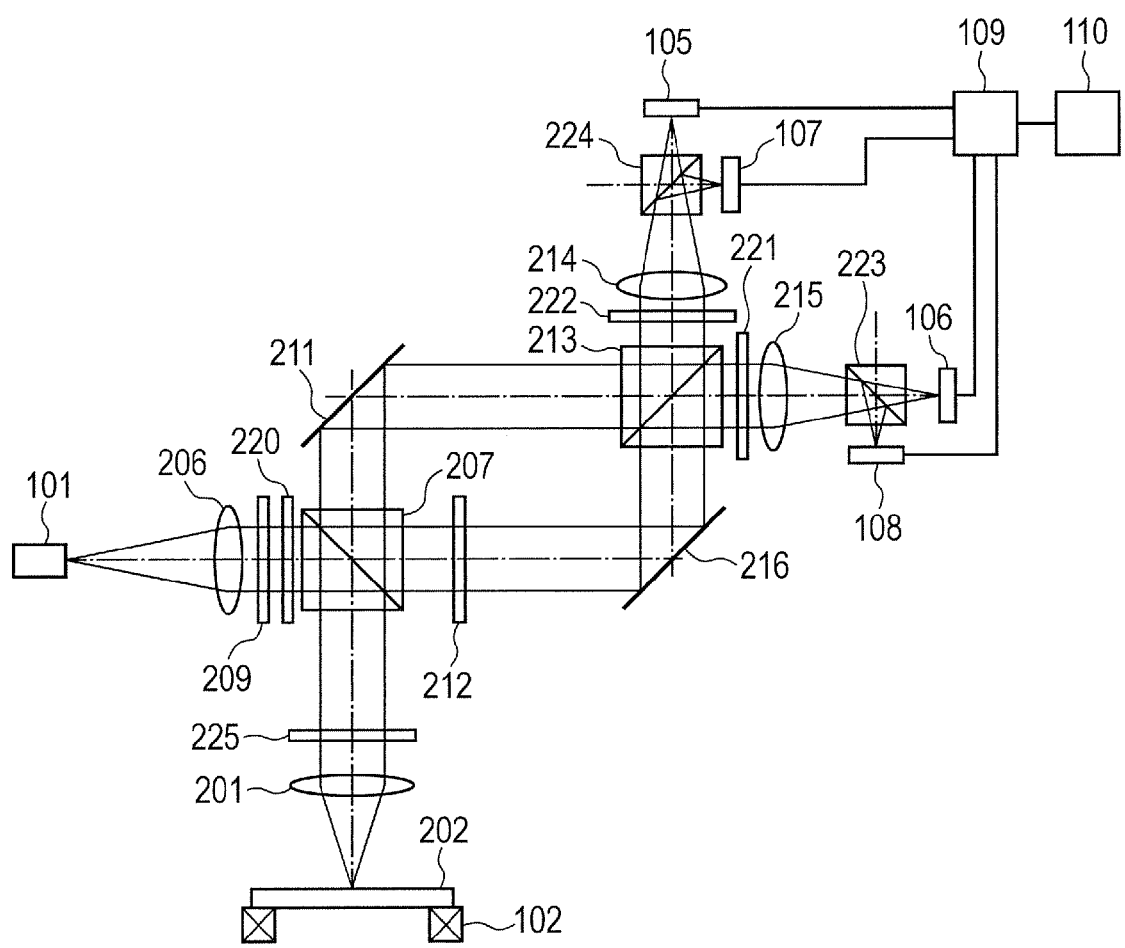
FIG. 5 shows an optical system according to the present invention.
Figure 6:
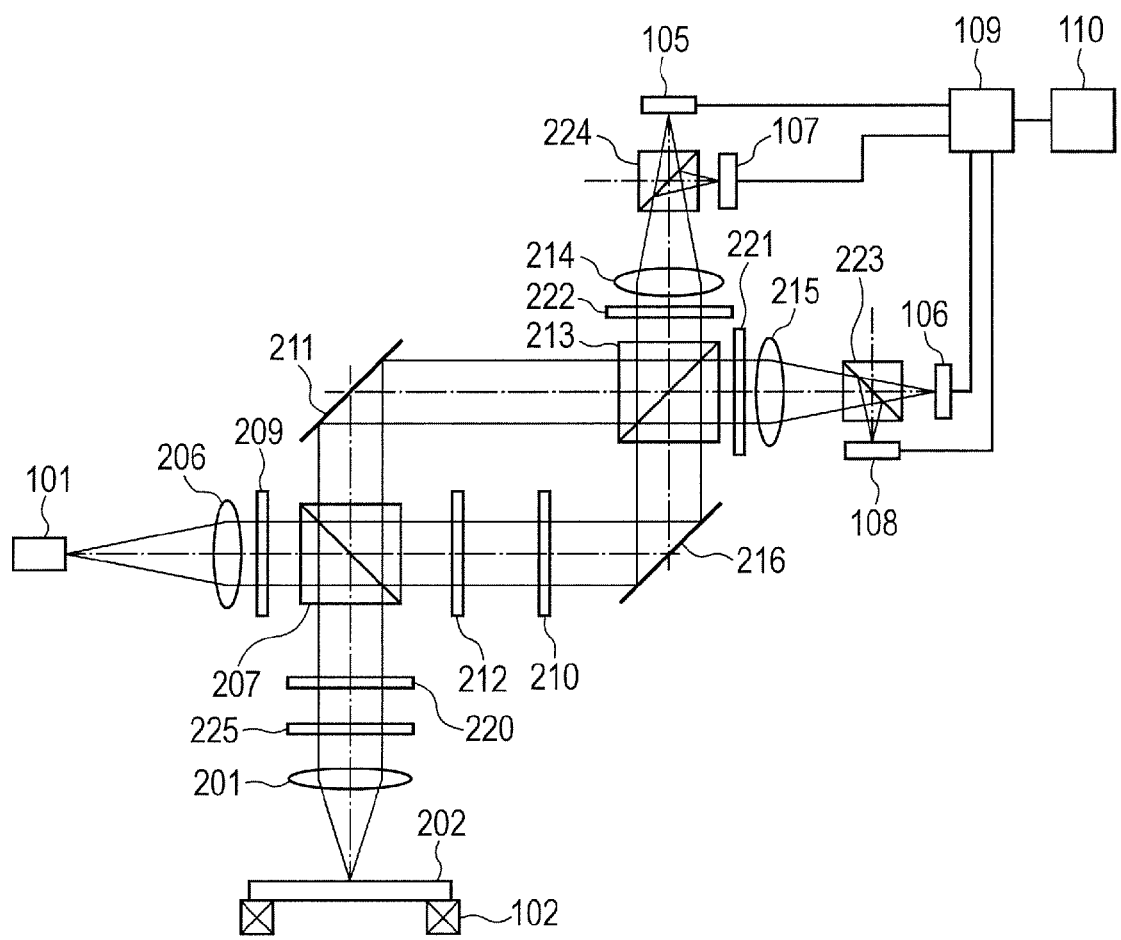
FIG. 6 shows an optical system according to the present invention.

FIG. 5 and FIG. 6 show a light shielding plate disposed in an optical path of the irradiation light directed toward the observation object. In FIG. 5, the light shielding plate 220 is inserted just before the polarization beam splitter 207. Effect of the light shielding plate remains effective to a beam which turns to the reference light after having passed the polarization beam splitter 207. However, no light shielding plate is disposed for a light reflected from the observation object. With a shielding plate disposed in the optical path of a light irradiated to the observation object, the focal depth can be increased and thereby the resolution can be improved. A light shielding plate 220 shown in FIG. 6 is disposed between the polarization beam splitter 207 and the observation object 202. Therefore, the light shielding plate acts on both a light irradiated toward the observation object and a light reflected from the observation object. In this case, a shielding plate is also disposed in the optical path of a light irradiated toward the observation object, such that the focal depth can be increased and a clear image can be obtained even when a focal point shift occurs on the observation object. 210 represents a darkening filter configured to adjust intensity of the reference light.

According to the present embodiment, an optical filter shielding the light in the central part thereof is used. In this case, transmittance of the light is 0% at a central part and 100% at a peripheral part thereof, so that the transmittance changes sharply at a boundary of the light shielding area. Other optical filters configured to gradually change the transmittance from a central part to a peripheral part thereof may be used.

Second Embodiment

Figure 7:
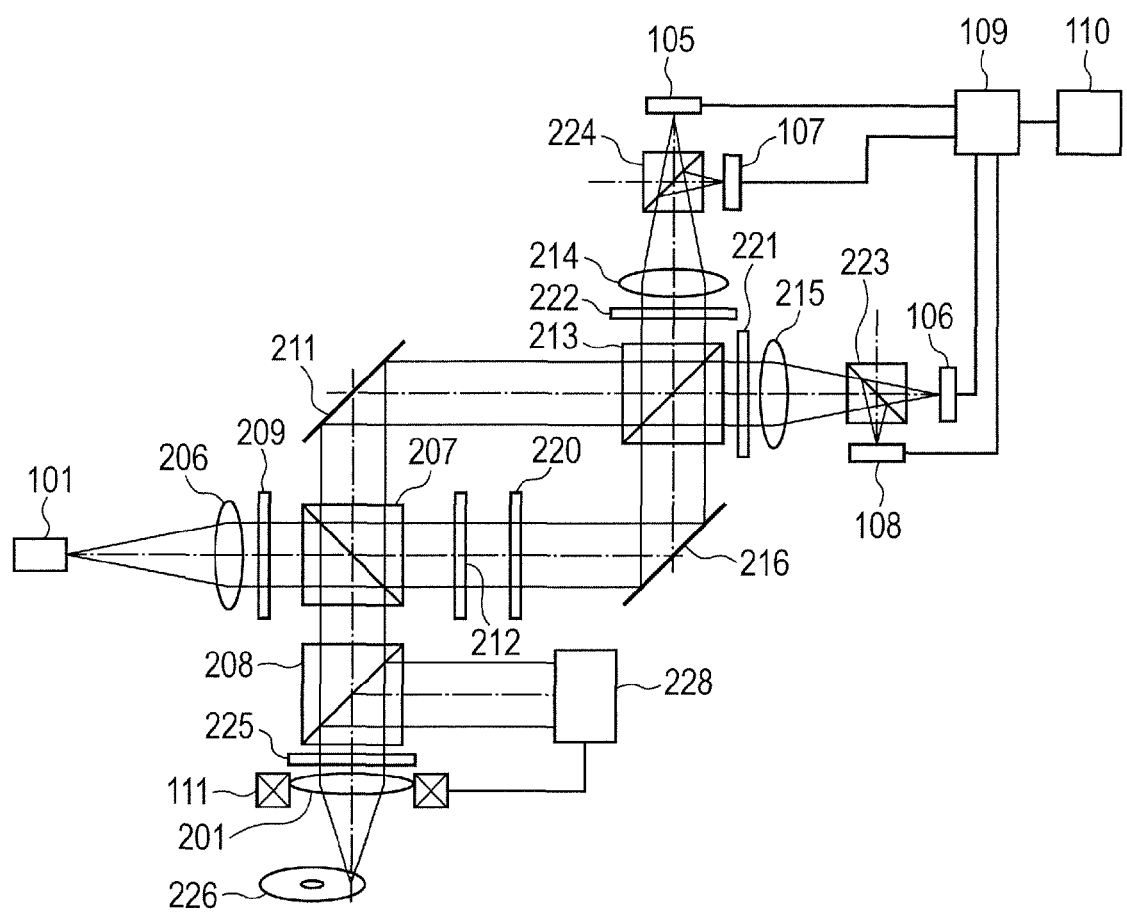
FIG. 7 shows an optical system of a light pickup device according to the present invention.
Figure 8:
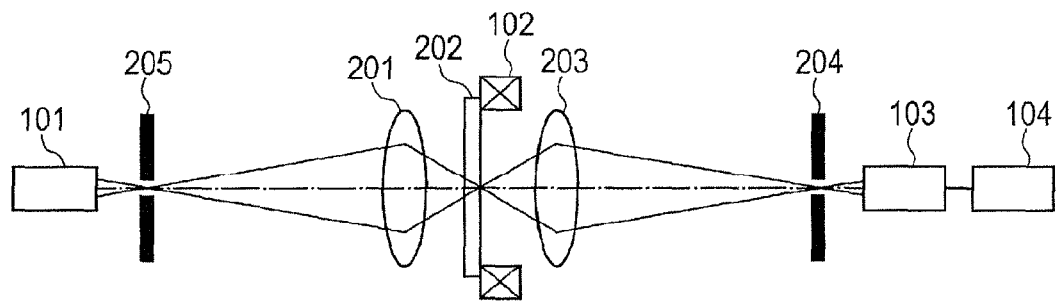
FIG. 8 shows an optical system of a transmission type confocal scanning microscope.
Figure 9:
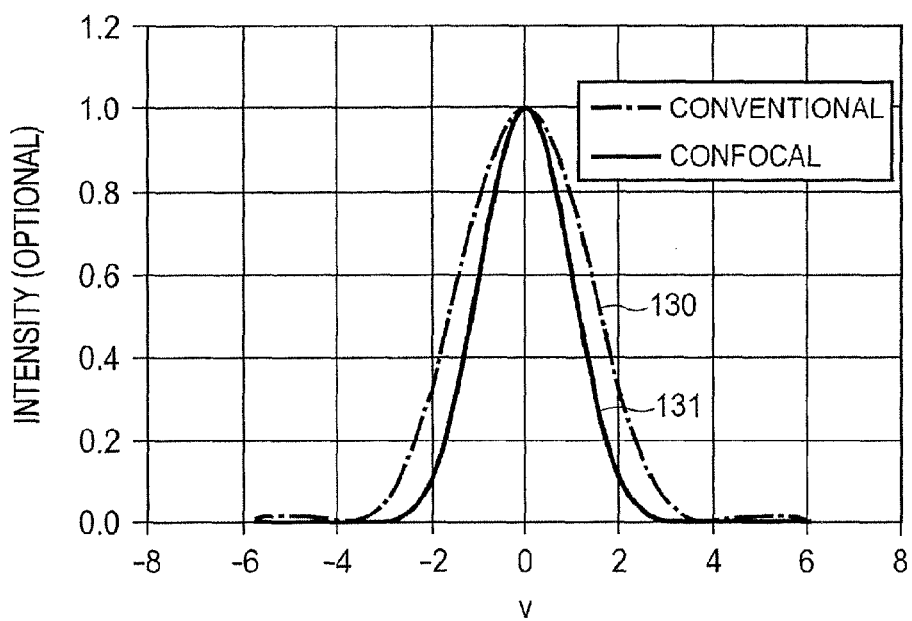
FIG. 9 shows point spread functions of a conventional optical microscope and a confocal scanning microscope.
Figure 10:
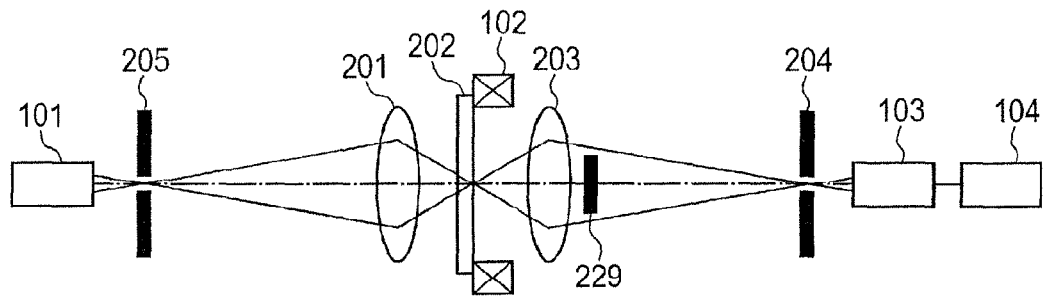
FIG. 10 shows an optical system according to the non-patent document (C. J. R. Sheppard and A. Choudhury, "Image Formation in the Scanning Microscope", Opt. Acta, Vol. 24, 1051-1073 (1977))

FIG. 7 shows a pickup optical system of an optical disc device using an optical system according to the present invention. Components according to the present embodiment shown in FIG. 7 with reference numerals same as those in FIG. 1 have same functions. A laser beam emitted from a light source 101 is collimated, and thereafter, an s-polarized light is reflected by a polarization beam splitter 207 and passes through a half beam splitter 208. The light, which has passed through the half beam splitter, is focused onto an optical disk 226 through an objective lens 201. The optical disk is rotatably fixed to a rotating body. A light reflected from the optical disk returns to the half beam splitter 208, where the light is split to two. A transmitted light directed toward the polarization beam splitter 207 is used for generating a data signal.

Figure 13:
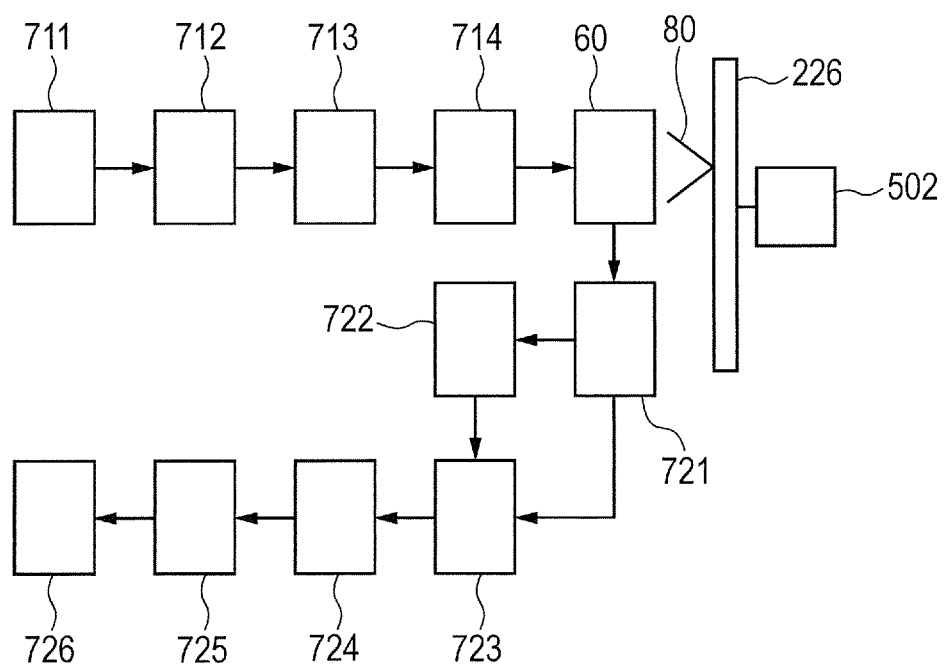
FIG. 13 shows a flow of signal processing when the optical apparatus is applied to an optical disc.

An interference optical system downstream the polarization beam splitter 207 is same as FIG. 1, and a signal of a high resolution is generated by a calculator 109. This signal is processed by an electronic circuit to a data signal. Signal processing in the electronic circuit is schematically described with reference to FIG. 13. Circuits 711 to 714 are provided to record data into the optical disk 226. An optical system other than the electronic circuit shown in FIG. 7 is represented by 60. 711 represents an error correction encoding circuit configured to add a error correction code to data. 712 represents a record encoding circuit configured to modulate data by the 1-7PP modulation. 713 represents a record compensation circuit configured to generate pulse for writing appropriate to a mark length. According to a generated pulse sequence, a semiconductor drive circuit 714 drives the laser light source 101 shown in FIG. 7 to modulate a laser light 80 emitted from the objective lens. Marks having different reflection ratios depending on the laser light are formed on an optical disk 226 rotated and driven by a motor 502.

Circuits 721 to 726 are provided to read out data. A data signal of a high resolution is input into an equalizer 721 to improve the signal to noise ratio in the vicinity of a region having a shortest mark length. This signal is input into a PLL circuit 722 to extract a clock. Further, the data signal processed by the equalizer is digitalized by an A-D converter 723 at a timing of the extracted clock. 724 represents a PRML (Partial Response Maximum Likelihood) signal processing circuit configured to perform Viterbi decoding. A record decoding circuit 725 decodes data in accordance with a modulation rule of the 1-7PP modulation, and an error correction circuit 726 restores data.

A light reflected by the half beam splitter 208 shown in FIG. 7 is processed by a control signal generation optical system 228, and a tracking error signal and a focus error signal are generated. These signals are fed back to an actuator 111 for position control of the objective lens so as to allow position control of the irradiated laser beam on the disk.

Figure 20:
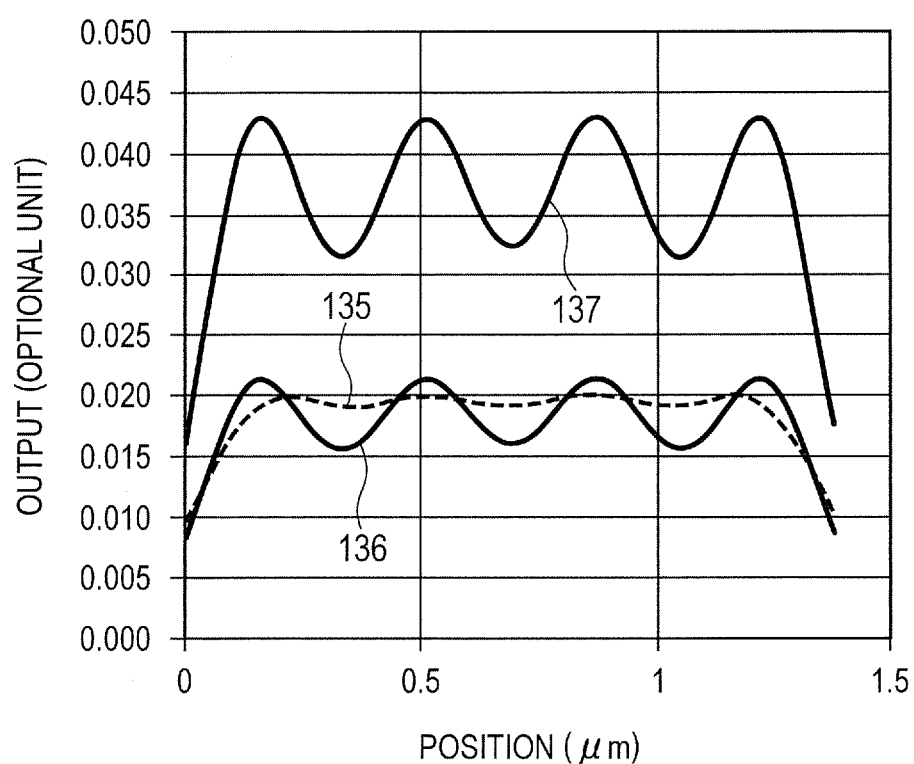
FIG. 20 shows variation of output signals from marked rows according to optical systems of the present invention.

FIG. 20 shows signal variations when marks written in the optical disk were read. Calculated signals are provided by the calculation device 109. Four marks of 0.13 µm long and 0.22 µm wide are spaced by 0.13 µm in a rotational direction of the optical disk. The reflectance of the mark and space is 90% and 1% respectively, and the laser beam passes through a center of the mark. Parameters of the optical system are same as those used in the calculation of FIG. 11. 136 represents an output variation when the reference light was shielded in an 80% region from a center thereof. 137 represents an output variation when intensity of the reference light was doubled. Doubling intensity of the reference light results in doubling the output, whereby the signal to noise ratio is improved. For the purpose of comparison, an output variation in a standard optical system is shown by a dashed line 135. It is understood that in the standard optical system, an intensity modulation by marks relative to average output at marked positions is smaller than that of the present invention.

Third Embodiment

Figure 14:
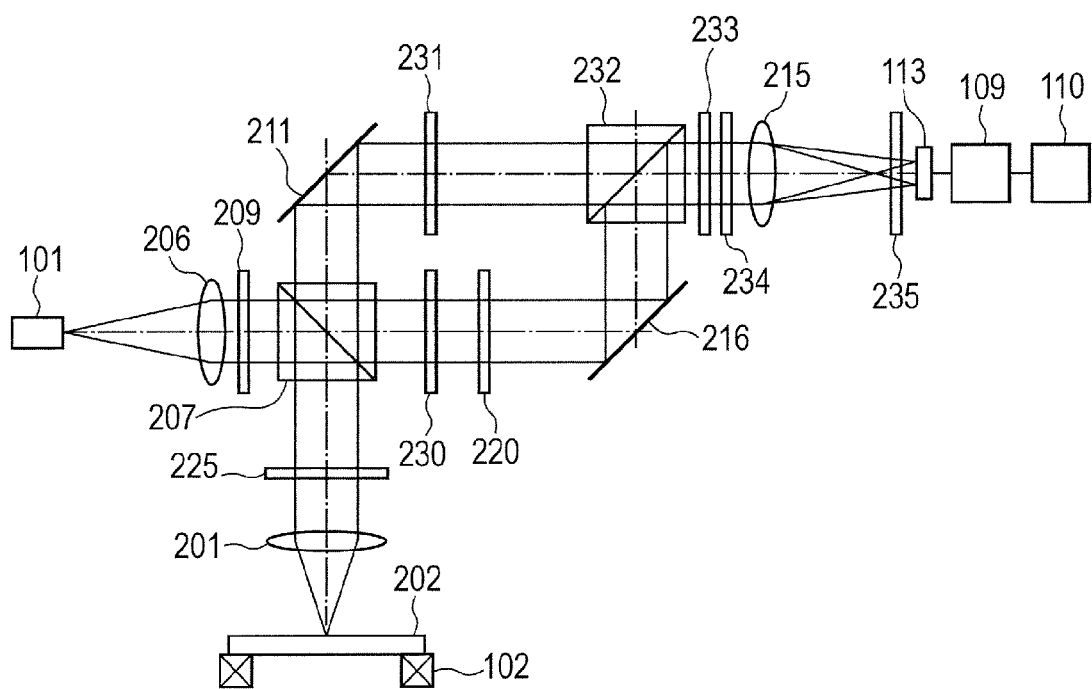
FIG. 14 shows an optical system according to the present invention.
Figure 15:
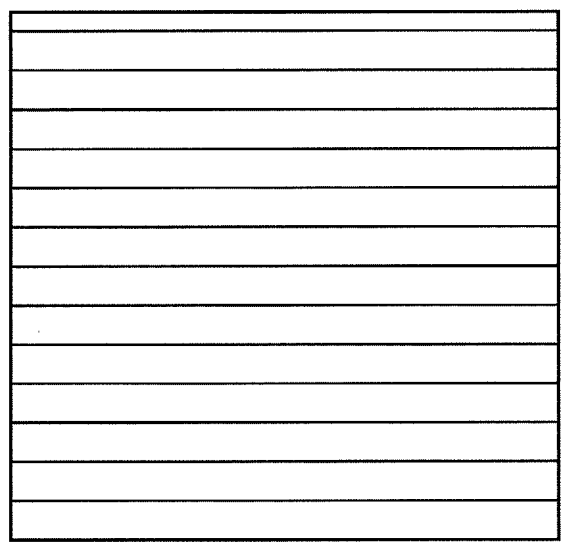
FIG. 15 shows non-polarization diffraction gratings.
Figure 16:
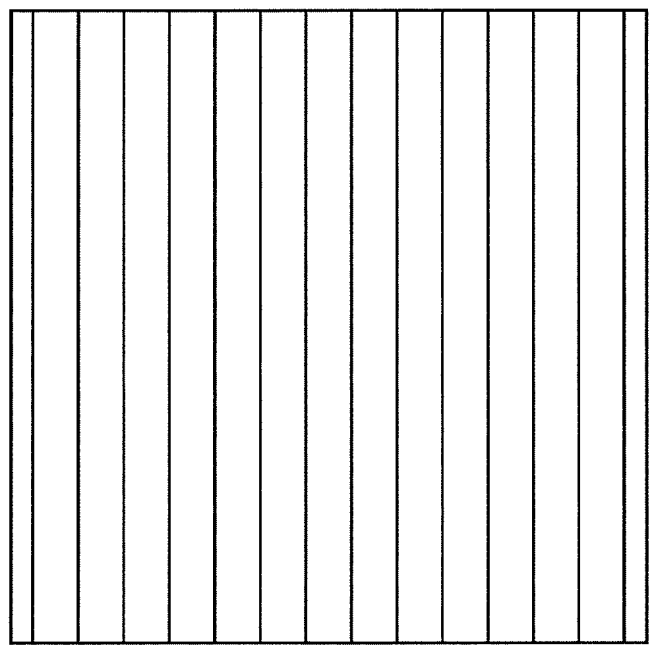
FIG. 16 shows non-polarization diffraction gratings.
Figure 17:
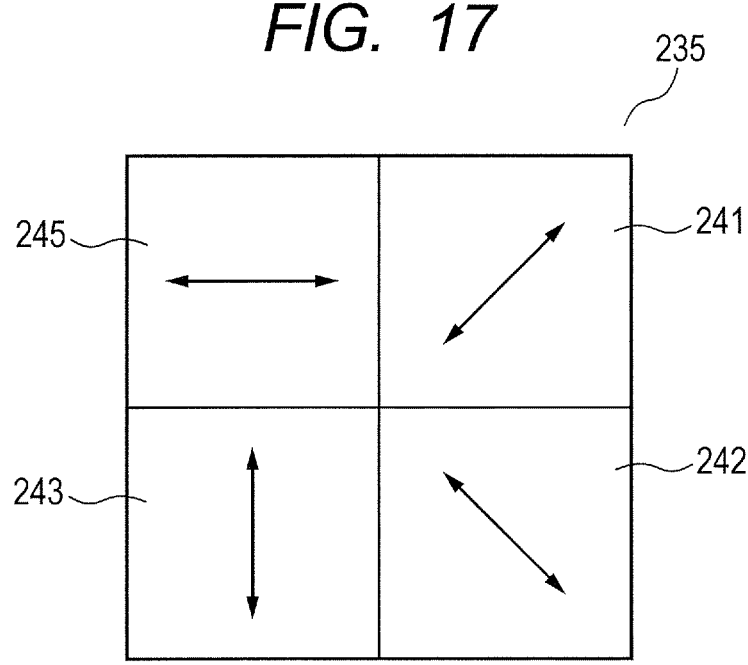
FIG. 17 shows quartered linear polarizers and optical axes thereof.
Figure 18:
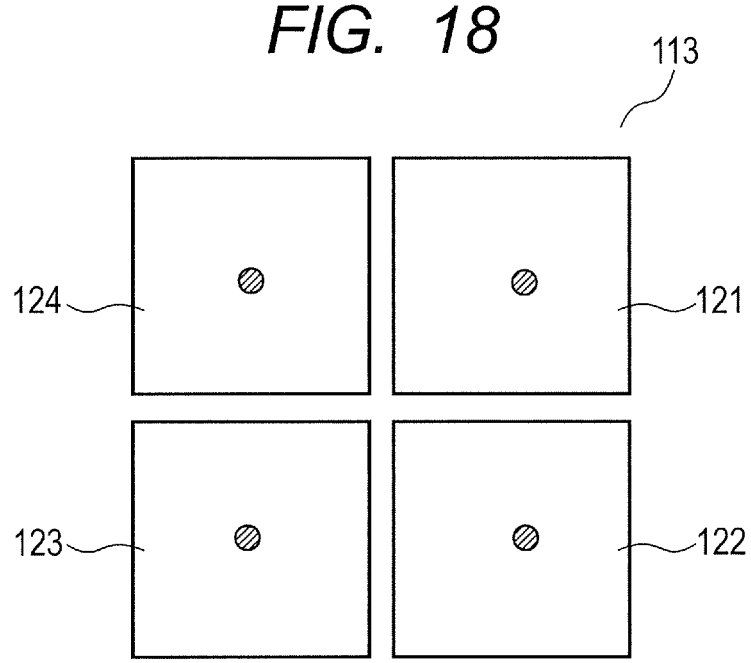
FIG. 18 shows a quartered detectors.

FIG. 14 shows an embodiment which uses a polarization different from the first embodiment. An optical system from the laser light source 101 to the polarization beam splitter 207 is same. The reference light, which has passed through the polarization beam splitter 207 directly from the light source, is converted to a right circularly polarized light by a λ/4 plate 230 and passes through a shielding plate 220. The reference light is reflected by a reflecting mirror 216 and enters a circular polarization beam splitter 232. On the other hand, a light reflected by the polarization beam splitter 207 and focused onto the observation object turns a p-polarized light when returned to the polarization beam splitter 207. Accordingly, the light passes through the polarization beam splitter 207. The light is reflected by a reflecting mirror 211 and converted to a left circular polarized light by a λ/4 plate 231. The left circular polarized light passes through a circular polarization beam splitter 232 and interferes with the right circular polarized light. Superposed right polarized and left polarized lights pass through non-polarization diffraction gratings 233 and 234. FIG. 15 and FIG. 16 show directions of grooves of non-polarization diffraction grating 233 and 234. Since directions of grooves in both gratings are orthogonal to each other, diffraction planes of high-order diffracted lights of ±1 order or higher are orthogonal to each other. The shape of the grooves is designed so as to become larger by a ±1 order light with a same intensity and become smaller by a diffracted light of 0 order or ±2 order or more. The pitch of the grooves is designed such that the light enters a detector described later. The light, which has passed through the non-polarization diffraction grating, is split to four and focused onto a quartered detector 113 by a condenser lens 215 shown in FIG. 14. The four beams are formed by an effect that two non-polarization diffraction gratings acting to split a beam to two ±1 order lights are superposed with directions of diffraction planes different from each other. A quartered linear polarizer 235 is disposed in front of a detector. Optical axes of linear polarizers 245, 241, 243 and 242 are directed at the angle of 0 degree, 45 degrees, 90 degrees and −45 degrees respectively. Each of the four split beams passes through a linear polarizer thereof and detected by a quartered detector of the detector 113. FIG. 18 shows surface shapes of detectors of the quartered detector 113. A light, which has passed through the linear polarizer 245, enters a detector 124. A light, which has passed through the linear polarizer 241, enters a detector 121. A light, which has passed the linear polarizer 243, enters a detector 123. A light, which has passed the linear polarizer 242, enters a detector 122. A black circle at the center of respective detectors indicates a focused state of the light. Assuming that a differential signal of outputs between detectors 124 and 123 is Ic, $Ic=\alpha|A|\cdot|R|\cos(\theta)$. And, assuming that a differential signal of outputs between detectors 121 and 122 is Is, Is is expressed as $Is=\alpha|A|\cdot|R|\sin(\theta)$. Accordingly, similarly with the first embodiment, the intensity signal of a high resolution can be obtained by calculating the formula of $I=Ic^2+Is^2=\alpha^2|A|^2|R|^2$ in the electronic circuit 109. The intensity signal of high resolution is displayed as an image on a display device 110.

Fourth Embodiment

Figure 19:
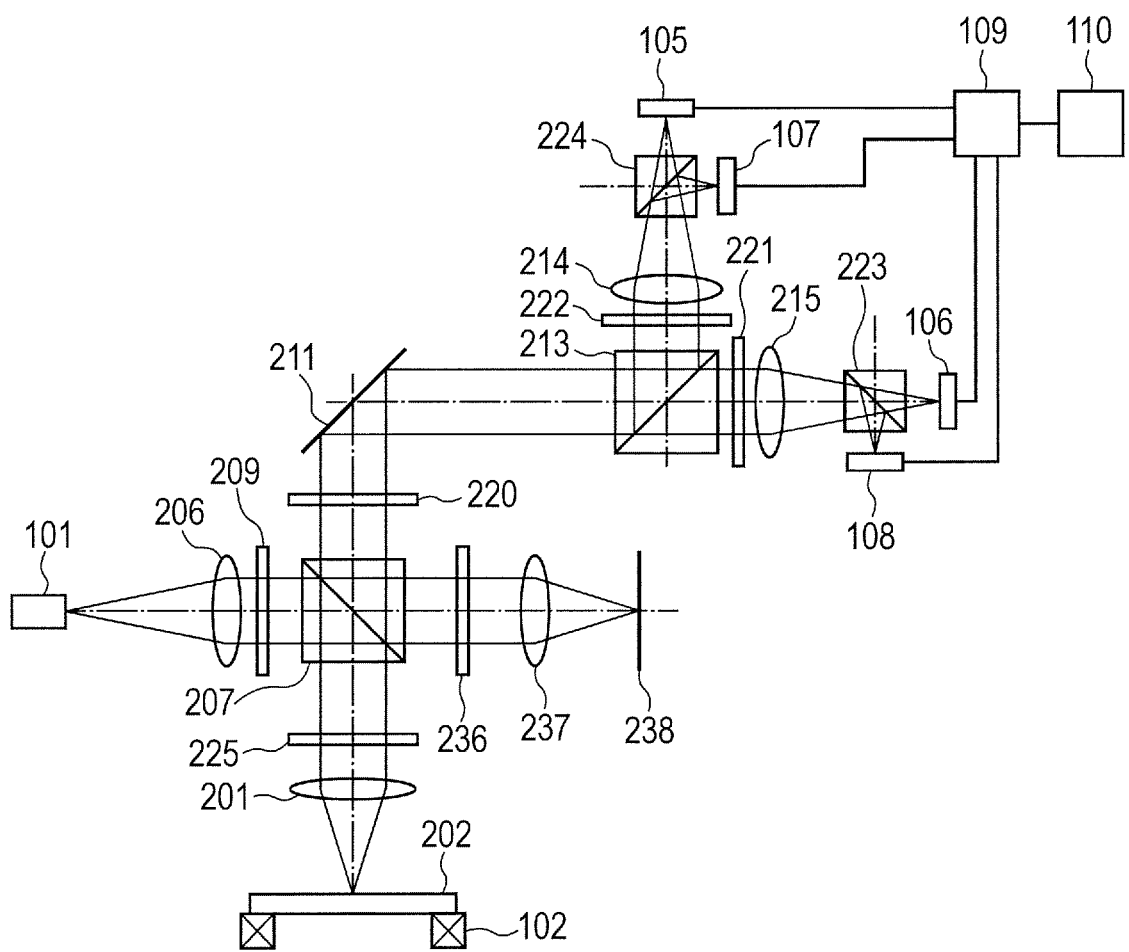
FIG. 19 shows an optical system according to the present invention.

According to an embodiment shown in FIG. 19, an optical system configured to return the reference light by a reflecting mirror is adopted. The optical system allows a long optical path common to the reference light and a light reflected from the observation object, so that effects on an interference optical system by external disturbance such as air fluctuation can be reduced.

A laser light from a laser light source 101, which has been collimated, is split to two according to the polarizing direction by a polarization beam splitter 207. An s-polarized light is reflected and directed toward an observation object 202. A light reflected from the observation object passes through a λ/4 plate 225 two times and thereby turns a p-polarized light and passes through the polarization beam splitter 207. A p-polarized light, which enters the polarization beam splitter 207 from the light source, passes through the polarization beam splitter 207 and is converted to a circularly polarized light by a λ/4 plate 236. Next, the light is focused onto a reflecting mirror 238 at a focal position by a convex lens 237 having an effective diameter and NA same as the objective lens 201. The light reflected by the reflecting mirror 238 returns to the convex lens 237 and passes through the λ/4 plate, whereby the light turns an s-polarized light and is reflected by the polarization beam splitter 207. Consequently, two lights including the p-polarized light from the observation object and the s-polarized light reflected by the reflecting mirror 238 travel from the polarization beam splitter 207 to a light shielding plate 220 and interfere with each other. Both beams are reflected by a reflecting mirror 211 and travel toward a beam splitter 213. Beams split to two by the beam splitter 213 respectively pass through a wavelength plate and a condenser lens and thereafter are split to two by a polarization beam splitter. Similarly with the first embodiment, an observed image of a high resolution is displayed on the display unit 110 by using signals of these four detectors.

According to the first, second and fourth embodiments, a synthetic light formed by superposing the reference light and a detected light is split to four. However, the interference component may be also calculated by splitting the light to three, although a complicated calculation is need.

Further, although all of the embodiments are described about interference optical systems using a light reflected from an irradiated object, similar effects can be obtained by using a light transmitting through the irradiated object, but in an optical system of a different configuration.

The present invention may be applied to not only an apparatus acquiring an image of a high resolution but also a light pickup reading an optical disk of a high density.

What is claimed is:

1. An optical apparatus comprising:
   a light source;
   a splitting optical system configured to split a light from the light source to a first light and a second light;
   a focusing optical system configured to focus the split first light onto an observation object and configured not to focus the split second light onto the observation object;
   a detection optical system configured to detect a detected light of a light reflected by the observation object or a light passing therethrough;
   a polarization optical element configured to polarize the detected light in a state different from the second light;
   a first optical system configured to superpose the detected light and the second light;
   a second optical system configured to split a superposed synthetic response light, the superposed synthetic response light being utilized to measure the observation object under an interference condition;
   a polarization filter disposed in an optical path of the synthetic response light;
   a detector configured to detect split synthetic response lights respectively;
   an optical filter disposed in an optical path of the second light, the optical filter being a spatial optical filter having a constant shape and having a light shielding region to shield a selected region of the second light from the first optical system and allow a remaining region of the second light to be superposed by the first optical system;
   an electronic circuit configured to process signals from respective detectors; and
   a display device configured to display output from the electronic circuit.

2. The optical apparatus according to claim 1, wherein the detected light is s-polarized, and the second light is p-polarized.

3. The optical apparatus according to claim 1, wherein the detected light is right circularly polarized, and the second light is left circularly polarized.

4. The optical apparatus according to claim 1, wherein the selected region is a central region of the second light.

5. The optical apparatus according to claim 1, wherein coherence length of the laser light source is about 5 mm or more.

6. The optical apparatus according to claim 1, further comprising an optical element configured to change a light amount ratio between the first light and the second light.

7. The optical apparatus according to claim 6, wherein the optical element provides a light amount of the second light larger than a light amount of the first light.

8. The optical apparatus according to claim 1, wherein the remaining region is a peripheral region of the second light.

9. The optical apparatus according to claim 1, wherein the light shielding region has a radius of at least 70% of an effective diameter of the second light.

10. An optical apparatus comprising:
    a light source;
    a splitting optical system configured to split a light from the light source to a first light and a second light;
    a focusing optical system configured to focus the split first light onto an optical disk and configured not to focus the split second light onto the optical disk;
    a detection optical system configured to detect a detected light from the optical disk;
    a polarization optical element configured to polarize the detected light and in a state different from the second light;
    a first optical system configured to superpose the detected light and the second light;
    a second optical system configured to split a superposed synthetic-response light, the superposed synthetic response light being utilized to detect the detected light from the optical disk under an interference condition;
    a polarization filter disposed in an optical path of the synthetic response light;
    a detector configured to detect split synthetic response lights respectively;
    an optical filter disposed in an optical path of the second light, the optical filter being a spatial optical filter having a constant shape and having a light shielding region to shield a selected region of the second light from the first optical system and allow a remaining region of the second light to be superposed by the first optical system;
    an electronic circuit configured to calculate amplitude information by processing signals from respective detectors;
    a signal processing circuit configured to perform signal processing of output from the electronic circuit;
    a control signal generation optical system; and a control mechanism configured to control a light focusing and irradiating position onto the optical disk with a tracking error signal and a focus error signal output by the control signal generation optical system.

11. The optical apparatus according to claim 10, wherein the detected light is s-polarized, and the second light is p-polarized.

12. The optical apparatus according to claim 10, wherein the detected light is right circularly polarized, and the second light is left circularly polarized.

13. The optical apparatus according to claim 10, wherein the selected region is a central region of the second light.

14. The optical apparatus according to claim 10, wherein coherence length of the laser light source is about 5 mm or more.

15. The optical apparatus according to claim 10, further comprising an optical element configured to change a light amount ratio between the first light and the second light.

16. The optical apparatus according to claim 15, wherein the optical element provides a light amount of the second light larger than a light amount of the first light.

17. The optical apparatus according to claim 10, wherein the remaining region is a peripheral region of the second light.

18. The optical apparatus according to claim 10, wherein the light shielding region has a radius of at least 70% of an effective diameter of the second light.

* * * * *